United States Patent [19]

Schmidt

[11] Patent Number: 4,946,454
[45] Date of Patent: Aug. 7, 1990

[54] PERINEAL SHIELD AND DISCHARGE CONTAINMENT FLAP

[75] Inventor: Sheila A. Schmidt, Appleton, Wis.

[73] Assignee: Kimberly-Clark Corporation, Neenah, Wis.

[21] Appl. No.: 327,369

[22] Filed: Mar. 22, 1989

Related U.S. Application Data

[63] Continuation of Ser. No. 44,085, Apr. 29, 1987, abandoned.

[51] Int. Cl.⁵ .............................................. A61F 13/56
[52] U.S. Cl. ................................. 604/385.1; 604/386; 604/387
[58] Field of Search .................. 604/385.1, 385.2, 386, 604/387, 392, 393; D24/50

[56] References Cited

U.S. PATENT DOCUMENTS

| | | | |
|---|---|---|---|
| 1,451,643 | 4/1923 | Woody . | |
| 1,958,082 | 5/1934 | Ellinger . | |
| 2,059,956 | 11/1936 | MacGlashane . | |
| 2,092,346 | 9/1937 | Arone . | |
| 2,827,053 | 3/1958 | Gordon . | |
| 3,724,464 | 4/1973 | Enloe | 604/385.1 X |
| 3,968,798 | 7/1976 | Hokanson . | |
| 3,968,799 | 9/1976 | Schrading | 604/385.1 X |
| 3,978,861 | 9/1976 | Schaar | 604/385.1 |
| 4,037,602 | 7/1977 | Hawthorne | 604/385.1 X |
| 4,067,336 | 1/1978 | Johnson | 604/385.2 |
| 4,108,179 | 8/1978 | Schaar | 604/385.1 |
| 4,182,334 | 11/1980 | Johnson | 604/385.2 |
| 4,213,459 | 7/1980 | Sigl | 128/287 |
| 4,216,773 | 8/1980 | Ryan | 128/284 |
| 4,226,238 | 10/1980 | Bianco | 604/385.1 |
| 4,490,148 | 12/1984 | Beckeström | 604/385 |
| 4,496,359 | 1/1985 | Pigneol | 604/386 |
| 4,519,800 | 5/1985 | Merry | 604/385 |

FOREIGN PATENT DOCUMENTS 0724836 1/1966 Canada ............................ 604/385.1
1520018 8/1978 United Kingdom .

OTHER PUBLICATIONS

WO 83/04178, Mitrani, 6/1983.

Primary Examiner—Carl D. Price
Attorney, Agent, or Firm—Douglas L. Miller; John L. Chiatalas; Thomas J. Mielke

[57] ABSTRACT

A perineal shield and discharge containment device comprises a sheet of flexible material adapted for folding into a configuration which will closely conform to the perineal contours of the human body. Fold lines radiate outwardly from a common point disposed on the longitudinal center line of the sheet material. When folded as prescribed, the sheet material forms a partial funnel-shape portion and a pocket having its deepest point generally located at the common point.

17 Claims, 4 Drawing Sheets

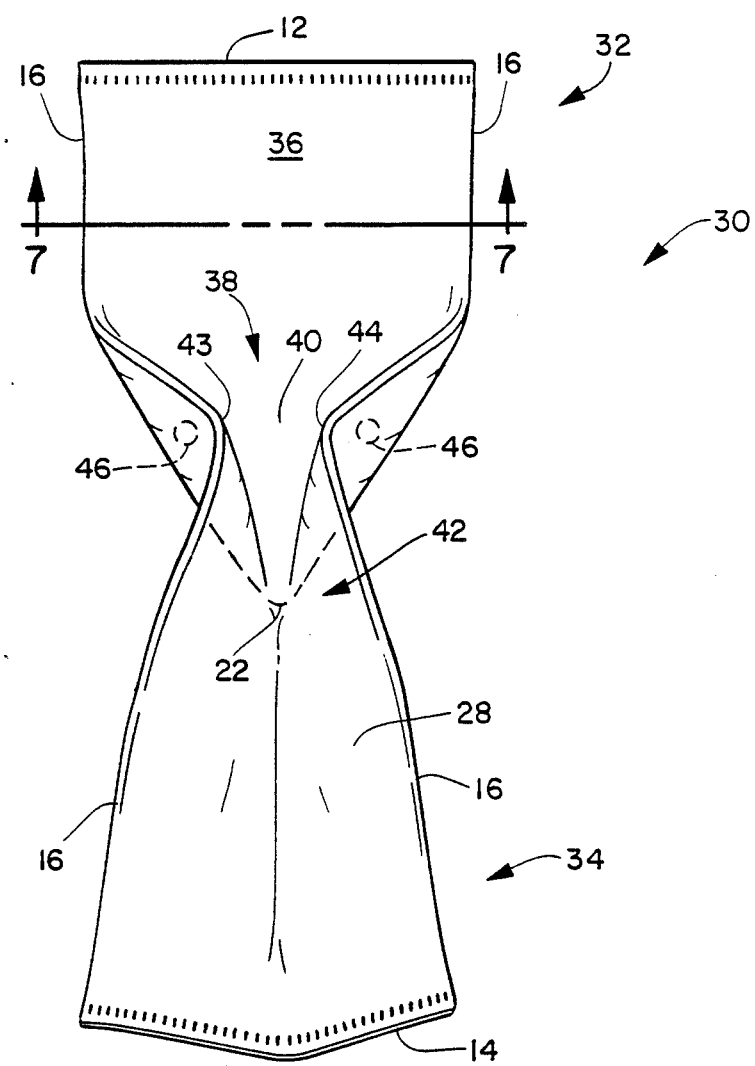
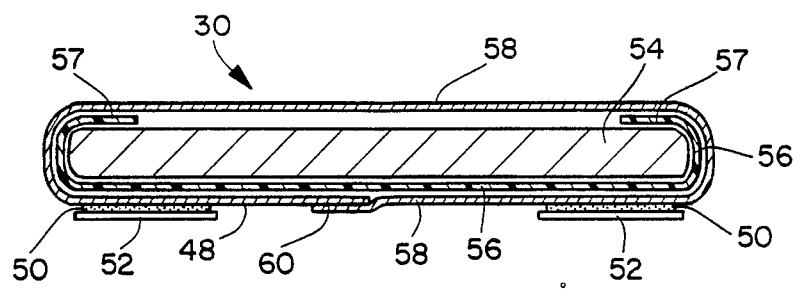
FIG. 5
FIG. 7

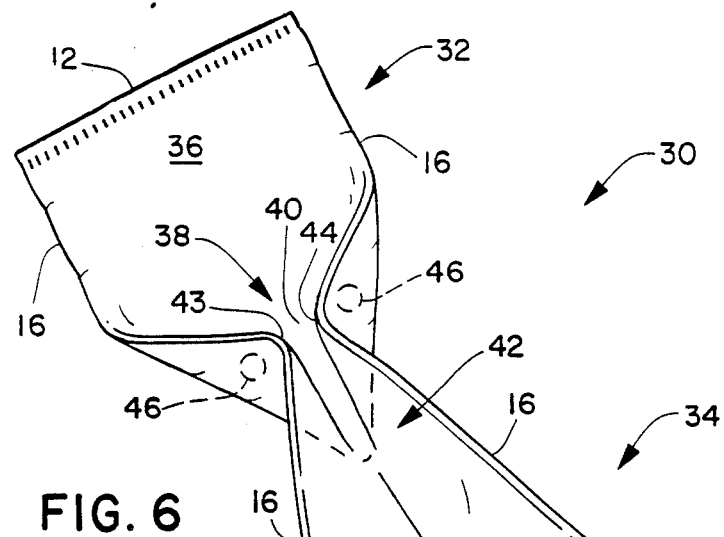
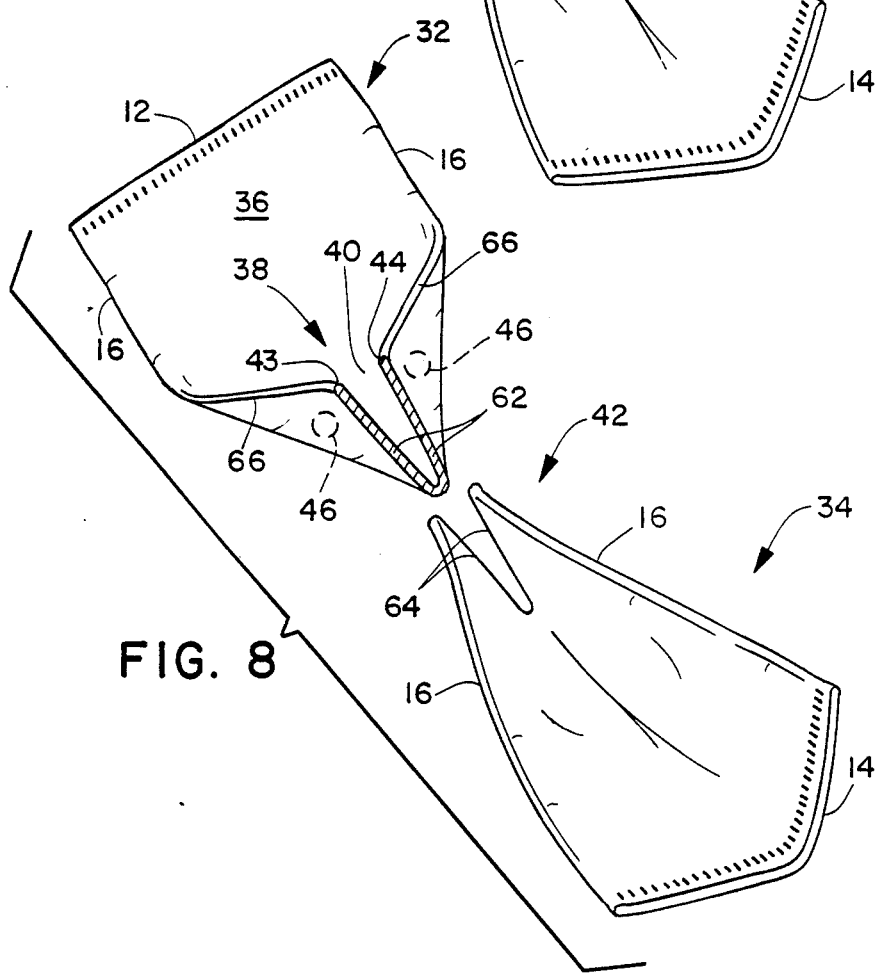

PERINEAL SHIELD AND DISCHARGE CONTAINMENT FLAP

This is a continuation of co-pending application Ser. No. 07/044,085 filed on Apr. 29, 1987.

BACKGROUND OF THE INVENTION

This invention pertains to a fluid containment device, and more particularly to a perineal shield and discharge containment device for absorbing and containing various body discharge.

The prior art includes many structures relating to perineal protective devices, such as garment shields, drip containment or dribble cups, sanitary napkins, diapers, incontinent pads and the like. Such devices range from very thin material for protecting against garment stains, which might otherwise result from small amounts of involuntary fluid discharge, to pads having sufficient capacity to absorb the full flow of menstrual fluid discharge, to still heavier pads for infant diapering and for collecting, absorbing and retaining the entire discharge of adult incontinence.

Various shapes have been devised in an attempt to obtain good body conformance, leakage prevention and comfort. While many are designed for reuse and are made from washable fabrics, the most recent developments have been directed to disposable materials, including nonwoven webs, thin plastic films and thick pads of absorbent fibers, in particular, air-formed pads of wood cellulose fibers. A major difficulty with most of the disposable materials is that they do not have the drapeability of more permanent cloth-like material and therefore will not conform well to the body, especially when made thick enough to provide the absorbent capacity needed for catamenial and diapering uses.

Various attempts have been made to obtain conformity by selecting particular fold geometries. While many of these obtain a good fit when first applied, they do not have the ability to move with changing body configurations. As a result, the material located between the thighs is often crushed by leg pressure soon after application, thereby losing its initial conformance, which results in gaps between the protective device and the body, or causes discomfort because of rubbing and/or chafing contact between the device and the body.

SUMMARY OF THE INVENTION

The present invention provides an improved perineal shield and discharge containment device that provides improved comfort and improved containment characteristics, and which is adaptable to be used in one form as a relatively thin garment protector, to another form as an absorbent pad capable of containing full-discharge incontinence.

In one form of the invention, there is provided a perineal shield and discharge containment device comprising a sheet of flexible material defined by a top bodyside surface, a bottom surface, a front edge, a back edge and two side edges; the sheet being provided with a plurality of pre-established fold lines along which the sheet is folded prior to use; the fold lines comprising: (a) a main fold line centrally and longitudinally disposed on the sheet, (b) a first pair of forwardly diverging fold lines originating on the main fold line and extending to the perimeter of the sheet and (c) a second pair of forwardly diverging fold lines disposed between the first pair of fold lines and the side edges of the sheet, this second pair of fold lines originating on the main fold line and extending to the perimeter of the sheet, the sheet being adapted for inward folding on the main fold line, inward folding on the first pair of forwardly diverging fold lines and outward folding on the second pair or forwardly diverging fold lines.

In another form of the invention, there is provided a method of making a perineal shield and discharge containment device comprising a sheet of flexible material having a top bodyside surface, a bottom surface, a front edge, a back edge and two side edges; comprising the steps of providing a main fold line centrally and longitudinally on the sheet, providing a first pair of forwardly diverging fold lines originating on the main fold line, providing a second pair of forwardly diverging fold lines disposed between the first pair of fold lines and the side edges of the sheet, folding inwardly on the main fold line, then folding inwardly on the first pair of forwardly diverging fold lines and thereafter folding outwardly on the second pair of forwardly diverging fold lines.

In yet another form of the present invention, there is provided a perineal shield and discharge containment device comprising a front panel and a back panel. The front panel includes a front edge and two side edges, portions of the side edges being disposed inwardly to form a partial funnel-shape portion in the front panel. The back panel includes a back edge and two side edges, the side edges being disposed inwardly to form the back panel into a trough-shape. The front panel and the back panel form a pocket near the neck of the funnel-shape portion, whereby the device contains body discharge in the pocket, and the funnel-shape portion delivers body discharge at the front panel to the pocket.

It is an object of the present invention to provide an improved perineal shield and discharge containment device.

Another object of the present invention is to provide a method of making an improved perineal shield and discharge containment device.

Further objects of the present invention will appear as the description proceeds.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein:

FIG. 5 is a top plan view;

FIG. 6 is a perspective view of the device;

FIG. 7 is a cross-sectional view taken along line 7—7 in FIG. 5 and viewed in the direction of the arrows; and FIG. 8 is a perspective view of another embodiment of the present invention.

DETAILED DESCRIPTION

Figure 2:
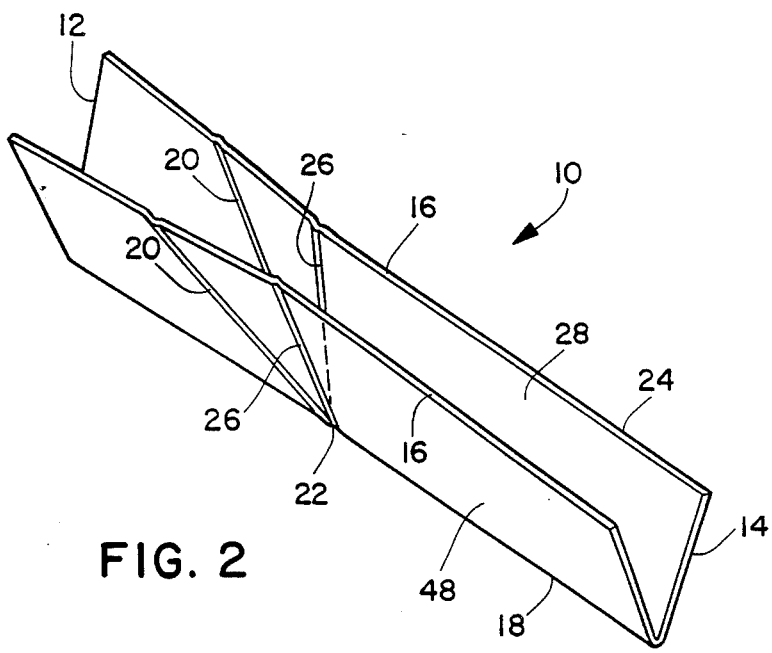
FIGS. 2-3 are perspective views showing the sequential folding of the sheet material.
Figure 3:
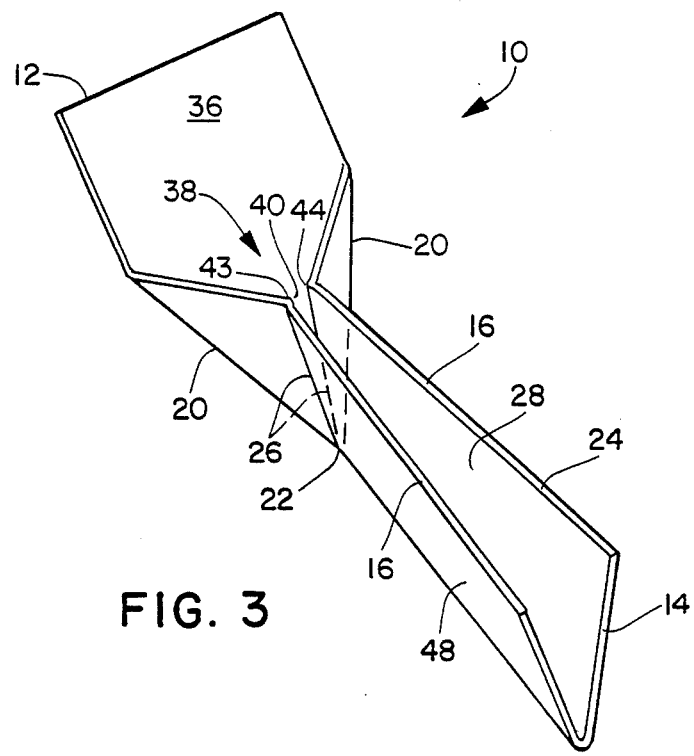
Figure 4:
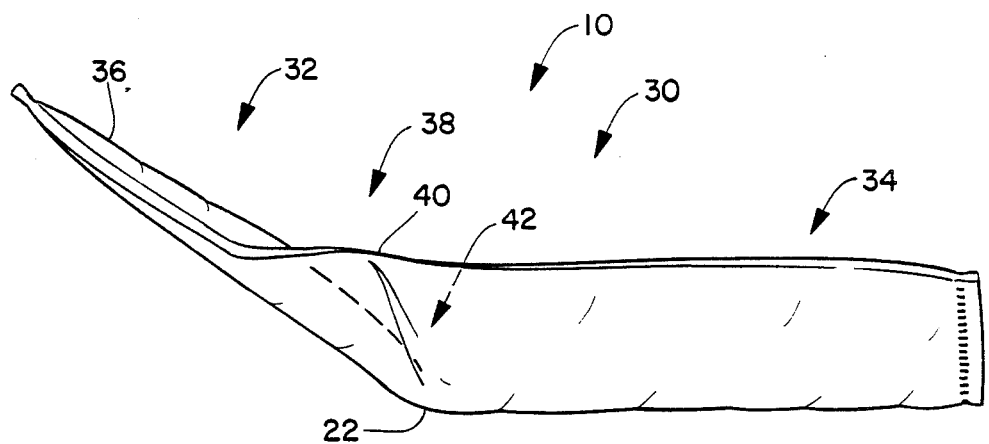
FIG. 4 is a side elevational view.

FIGS. 1-4 show a series of perspective views of a flexible material having pre-established fold lines in accordance with one embodiment of the present invention, first in its unfolded condition and then followed by sequential folding to a fully folded condition ready for use. In FIGS. 4 and 5, the folded views serve to illustrate both sheet 10 and a perineal shield and discharge containment device 30, which is more fully described below.

Figure 1:
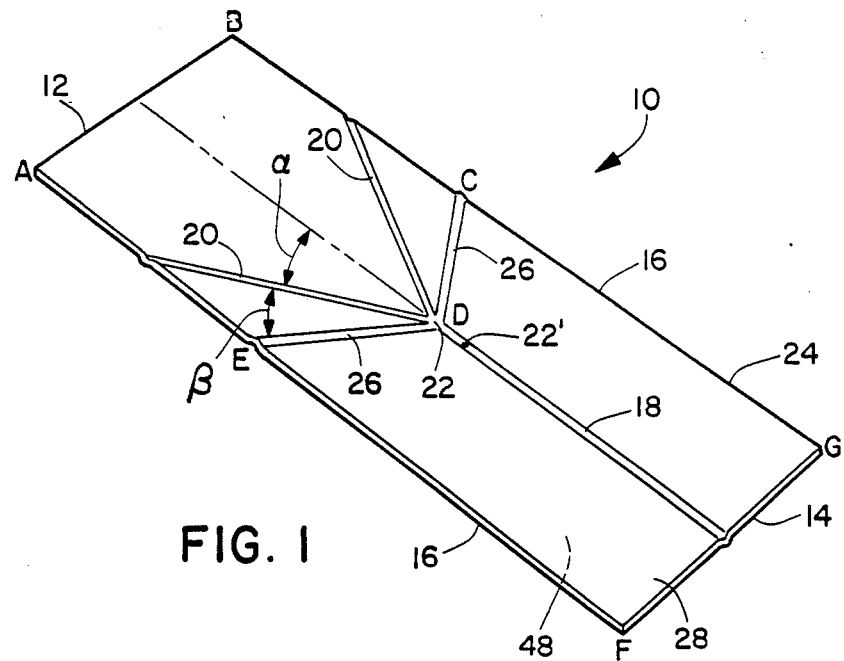
FIG. 1 is a top perspective view of a rectangular sheet of material showing the arrangement of the pre-established fold lines of one embodiment of the invention.

Referring to FIG. 1, an elongate rectangular sheet 10 of material having a front edge 12, back edge 14 and two side edges 16 is provided with a plurality of fold lines, including main fold line 18 centrally and longitudinally disposed along the major axis, a first pair of forwardly diverging fold lines 20 originating on main fold line 18 from common point 22 spaced inwardly from front edge 12 and extending to the sheet perimeter 24 at side edges 16, and a second pair of forwardly diverging fold lines 26 also originating at common point 22 and disposed in spaced arrangement between the first pair of forwardly diverging fold lines 20 and side edges 16 and terminating at side edges 16. Although described as common point 22, the location from which lines 20, 26 originate may indeed be a point, or may be a relatively small area as the thickness of sheet 10 increases. Thus, lines 20, 26 are to be understood as originating from a relatively small area in comparison to the total area of sheet 10.

In the folding sequence, FIG. 2 shows sheet 10 being folded inwardly on main fold line 18. FIG. 3 shows sheet 10 being folded inwardly on the first pair of forwardly diverging fold lines 20 and folded back outwardly on the second pair of forwardly diverging fold lines 26. In FIG. 4, sheet 10 is completely folded. From this point on, reference will be made to device 30, and that reference also includes sheet 10. Generally, sheet 10 would be used for very light to light discharge, while device 30 can be used for any type of discharge rate.

In FIG. 5, folded device 30 of FIG. 4 has been somewhat partially opened to expose top bodyside surface 28 to illustrate the configuration which perineal shield and discharge containment device 30 assumes as it is readied for positioning on the perineum. As illustrated, the partially opened device 30 has an upstanding front panel 32 and a back panel 34 which, for the sake of simplicity, can be said to meet in the area of common point 22. Front panel 32 includes a substantially flat portion 36 adjacent front edge 12 and a partial funnel-shape portion 38 formed by the folding along fold lines 20, 26. Funnel-shape portion 38 is described as being partial in that the folding along fold lines 20, 26 does not result in device 30 being completely closed, but rather resulting in an open or exposed neck 40 of funnel-shape portion 38. Regarding flat portion 36 of front panel 32, although the folding along main fold line 18 results in front panel 32, as well as back panel 34, being turned inwardly, the next two folds on the forwardly diverging fold lines 20, 26 cause the remote portion of front panel 32 to become substantially flat, thereby resulting in flat portion 36.

Back panel 34 is in the general shape of a trough, with its sides 16 generally converging from back edge 14 towards common point 22.

The folding that results in funnel-shape portion 38 of front panel 32 and the trough-shape of back panel 34 causes a pocket 42 to be formed, wherein the deepest or bottommost point of pocket 42 is located generally at common point 22.

Continuing to refer primarily to FIG. 5, along with FIG. 6, it can be seen that the inwardly-turned side edges 16 of front panel 32 form the funnel-shape portion 38 having the open or exposed neck 40, and that the open or exposed portion of neck 40 is identified by points 43, 44 and common point 22. Funnel-shape portion 38 serves to direct any fluid discharge directed thereat through neck 40 into pocket 42 for containment. One of the improved features of device 30 of the present invention is that the funnel-shape portion 38 prevents an unusually large fluid discharge from overflowing side edges 16.

Another key feature of device 30 is the longitudinal location of pocket 42. As can be seen in FIGS. 4, 5 and 6, pocket 42 is generally located centrally of device 30. This central location of pocket 42 disposes it generally at the mid-portion of the perineal area for proper collection and containment of body discharge.

Yet another key feature of device 30 is the position of neck 40 relative to the length of device 30, as measured when device 30 is flat, as illustrated in FIG. 1. Neck 40 is desirably spaced from front edge 12, a distance of about 15% to 40% of the total length of device 30. Preferably, the position of neck 40 is about 30% to about 40% of the total length of device 30 from front edge 12. Finally, the optimum position is 33% of the total length.

Referring to FIG. 1, common point 22 can be generally located near the mid-point of main fold line 18, with forwardly diverging fold lines 20, 26 emanating therefrom. By then folding along fold lines 18, 20, 26, device 30 will result wherein pocket 42 is generally centrally disposed relative to the total length of device 30, and neck 40 of funnel-shape portion 38 is positioned about 15% to about 40% of the total length of device 30 from front edge 12.

When properly worn, flat front portion 36 conforms to the generally smooth or flat lower abdominal region, and the narrow portion comprising funnel-shape portion 38 and pocket 42 comfortably fits in the perineal area. The portion of back panel 34 adjacent back edge 14 easily conforms to the buttocks of the wearer. This fold geometry resulting in funnel-shape portion 38 and pocket 42 permits device 30 to expand or contract by angular motion of the folds in response to leg pressure without crushing, thereby eliminating one source of discomfort and/or poor fit.

An infinite variety of shapes and sizes for device 30, as well as different angular relationships of the forwardly diverging fold lines and the location of common point 22 are possible without departing from the advantages or scope of the present invention. For example, in FIG. 1, angle alpha, which represents the angle between main fold line 18 and the first pair of fold lines 20, and angle beta, which represents the angle between fold lines 20, 26, can be varied as necessary or desired to obtain a particular geometry for funnel-shape portion 38 and pocket 42. Naturally, as the dimensions of device 30 vary, not only in length and width, but also in thickness, the general central location of common point 22, and the angular relationships between the fold lines 18, 20 and 26 will need to be altered in order to properly accommodate the use for which device 30 is intended. For example, these angular relationships and positions will tend to change when device 30 is configured and dimensioned for use as a particular device, such as a sanitary napkin, baby diaper, adult incontinent garment and the like. Also, since common point 22 may vary upon changing the dimensions of device 30, the location of pocket 42 will also vary, but pocket 42 will at least be located intermediate front edge 12 and back edge 14.

The present invention also contemplates fold lines 20, 26 as forwardly diverging from their own respective common points 22. The two common points 22 are generally closely spaced, such as common point 22 and common point 22' in FIG. 1. Common points 22, 22' are spaced apart generally no more than one inch.

The device 30 of the present invention may be made available to the user in either flat or pre-folded condition. When provided in flat condition, fold lines 18, 20 and 26 should be permanently scored, embossed or indented to facilitate folding by the user as the device is being readied for use. After folding, adhesive tape, spots or other securement means 46 may be applied between the folded areas or at overlapping edges to aid in retaining the folded condition.

Preferably, device 30 is prefolded for convenience to the user. In such an event, and as indicated above, it is preferably secured in the folded configuration by securement means 46, as illustrated in FIG. 5, or by some other suitable means such as double-faced tape, stitching, stapling or the like. When device 30 is prefolded, there is no need for the fold lines to be permanently scored, embossed or indented. The apparatus designed for making device 30 performs the correct folding technique and sequence on a relatively flat, unscored device 30.

Device 30 is preferably maintained in position by an undergarment to which device 30 is adhered. This can be accomplished by applying adhesive 50 (FIG. 7) on bottom surface 48, with a release material 52 covering the outermost surface of adhesive 50. Prior to use, release material 52 is removed and then device 30 secured or adhered in place with adhesive 50. This adhesive 50 can be in the form of one or more ribbons of adhesive running the longitudinal length of bottom surface 48 or a desired number of spots of adhesive applied to bottom surface 48. Finally, the securement of device 30 in an undergarment can be accomplished by applying a friction surface to bottom surface 48, such as providing bottom surface 48 with a series of lines of a spunbonded material or totally covering bottom surface 48 with the spunbonded material.

For some uses, as in the protection of garments from the staining which might otherwise be caused by light discharge, device 30 may comprise a single layer of material, and the material may be either absorbent or nonabsorbent. When discharge is expected to be light, it may, for example, be comprised of a thin sheet of plastic film such as polyethylene, polypropylene, vinyl or the like, which would serve primarily to shield but not absorb. However, for comfort, the film may be coated with a thin fiber layer on the top surface which could also be absorbent.

For use as a drip catcher or dribble cup, device 30 can be made of a thin plastic sheet with a thin layer or layers of absorbent material laminated to the top surface. Creped cellulose wadding tissues, nonwoven webs or thin air-formed and bonded batts are suitable for this purpose. Such a structure is also suitable for menstrual use during light flow, or in conjunction with tampons, or for use in garment protection when a hemorrhoidal condition exists.

Referring to FIG. 7, device 30 may be a multi-layered device including an absorbent batt 54 and a vapor pervious, liquid impervious liner 56, portions of which may overlap batt 54 to form baffles 57. Device 30 can also be a three-layered device including batt 54, breathable impervious liner 56 and a pervious liner 58 that can, as illustrated in FIG. 7, totally encompass batt 54 and impervious liner 56, or may just cover the top of baffles 57 and absorbent batt 54.

Absorbent batt 54 can be a wood pulp fluff, plies of cellulose tissue, a blend of wood pulp and synthetic fibers, foam materials and may include superabsorbent materials.

Vapor pervious, liquid impervious liner 56 can be made of a polymer, such as polypropylene or polyethylene, or copolymers such as ethylene methylacrylate, ethylene vinylacetate, ethylvinylacrylate and blends thereof that have micro-pores therein. Liner 56 can be a polymer or copolymer film with micro-pores, or a polymer or copolymer nonwoven material with micro-pores. Liner 56 can also be made of other suitable materials if they are vapor pervious and liquid impervious. Also, liner 56 could be made of a liquid-impervious-only material.

Pervious liner 58 can be an apertured plastic material or a spunbonded material, such as spunbonded polypropylene. As indicated in FIG. 5, when device 30 is multi-layered, front edge 12 and back edge 14 are sealed, such as by ultrasonic bonding, adhesives, stitching or the like.

In FIG. 7, pervious liner 58 totally encompasses absorbent batt 54 and impervious liner 56, and has a seam 60 disposed on the back thereof.

When device 30 is multi-layered, as illustrated in FIG. 7, baffles 57 work in conjunction with funnel-shape portion 38 to prevent the overflow of a heavy discharge of fluid over side edges 16, and deliver the fluid to pocket 42.

For general comfort purposes, the width of device 30 is preferably in the range of about 2 to about 10 inches, and the length is preferably in the range of about 6 to about 24 inches.

The above description of device 30 has been made with the assumption that it is a single component. However, device 30 can be a two-component device, wherein front panel 32 is one component and back panel 34 is the other component, as illustrated in FIG. 8. Referring also to FIG. 1, in conjunction with FIG. 8, front panel 32 can include that portion bounded by the points A, B, C, D and E, and back panel 34 can be that portion encompassed by points C, D, E, F and G. In this manner, front panel 32 comprises front edge 12, two side edges 16 and a first mating edge 62 (FIG. 8) that has an extending, generally V-shaped profile. Similarly, back panel 34 comprises back edge 14, two side edges 16 and a second mating edge 64 that has a recessed, generally V-shaped profile, which is complementary to the profile of first mating edge 62. Front panel 32, as illustrated in FIG. 8, is formed by inwardly turning respective adjacent portions 66 of side edges 16, thereby forming funnel-shape portion 38. Back panel 34 is formed as illustrated in FIG. 8, by inwardly turning or folding side edges 16, such that side edges 16 converge from back edge 14 toward second mating edge 64. The folding of front panel 32 and back panel 34 is accomplished in a manner so that first mating edge 62 and second mating edge 64 are complementary and can be joined together in any suitable manner.

The alternative embodiment of the present invention illustrated in FIG. 8 has certain advantages, such as allowing front panel 32 to be a multi-layered panel, and back panel 34 to be a differently multi-layered panel. For example, front panel 32 could be a two-layered panel, while back panel 34 could be a three-layered panel. Other various combinations are naturally possible.

The present invention provides an improved perineal shield and discharge containment device that provides for fluid discharge to be contained, while being absorbed in those embodiments having an absorption batt or other absorption medium. The improved perineal fit also allows device 30 to remain in place, with little or no shifting, during movement of the user, thereby minimizing distortion of the shape of device 30. The shape of device 30 further provides a fit that cradles the perineum to provide the discreteness and comfort desired of the user.

While this invention has been described as having a preferred embodiment, it will be understood that it is capable of further modifications. This application is therefore intended to cover any variations, uses, or adaptations of the invention following the general principles thereof, and including such departures from the present disclosure that come within known or customary practice in the art to which this invention pertains and fall within the limits of the appended claims.

What is claimed is:

1. A perineal shield and discharge containment device comprising: a sheet of flexible material in generally elongate form defined by a top body side surface, a bottom surface, a front edge, a back edge, and two side edges, said sheet being inwardly folded along a central longitudinal fold line such that portions of said body side surface on opposite sides of said central longitudinal fold line are brought closer together, said sheet further being inwardly folded along a pair of first diverging fold lines originating on said central longitudinal fold line at a first common point and extending from said first common point towards the front edge to said side edges such that portions of said body side surface on opposite sides of said first diverging fold lines are brought into contact, said sheet further being outwardly folded along a pair of second diverging fold lines disposed between said first pair of fold lines and said side edges, said second fold line originating at a second common point and extending from said second common point towards the front edge to said side edges such that portions of said bottom surface are brought closer together, said folded sheet defining a partial funnel-shaped portion having an open neck defined by the outward fold along said second fold line, said neck being spaced from said front edge a distance of about 15 percent to 40 percent of the total length of said device, said folded sheet further defining a generally centrally located pocket whereby said partial funnel-shaped portion serves to direct any fluid discharged directed thereat into said pocket.

2. The device of claim 1 wherein, said first and second common points coincide.

3. The device of claim 2 wherein said first and second common points are generally located near a midpoint of said central longitudinal fold line.

4. The device of claim 1 wherein said neck is spaced from said front edge a distance of about 30% to about 40% of the total length of said device.

5. The device of claim 4 wherein said neck is spaced from said front edge a distance of about 33% of the total length of said device.

6. The device of claim 1 wherein said pocket is generally located centrally of said device.

7. The device of claim 1 wherein said side edges of said device converge in a direction from said back edge toward said neck.

8. The device of claim 1 wherein said device has a width of from about 2 to 10 inches and a length of from about 6 to about 24 inches.

9. The device of claim 1 wherein said sheet of flexible material comprises a breathable impervious liner, a pervious liner and an absorbent batt.

10. The device of claim 1 wherein said sheet is secured in folded condition by securement means.

11. The device of claim 10 wherein said securement means include adhesive spots.

12. The device of claim 1 wherein said device further comprises an adhesive applied to said bottom surface for adhering said device to an undergarment.

13. The device of claim 1 wherein said first common point and said second common point are spaced from one another along said central longitudinal fold line.

14. The device of claim 13 wherein said first and second common points are spaced no more than one inch from one another.

15. A method of making a perineal shield and discharge containment device, said method comprising the following steps:
folding a sheet of flexible material having a generally elongate form defined by a top body side surface, a bottom surface, a front edge, a back edge, and two side edges, inwardly along a central longitudinal fold line such that portions of said body side surface on opposite sides of said central longitudinal fold line are brought closer together;
folding said sheet inwardly along a pair of first diverging fold lines originating on said central longitudinal fold line at a first common point and extending from said first common point towards the front edge to said side edges such that portions of said body side surface on opposite sides of said first diverging fold lines are brought into contact; and
folding said sheet outwardly along a pair of second diverging fold lines disposed between said first pair of fold lines and said side edges, said second fold line originating at a second common point and extending from said second common point towards said front edge to said side edges such that portions of said bottom surface are brought closer together; said folds being positioned such that said sheet defines a partial funnel-shaped portion having an open neck defined by the outward fold along said second fold line said neck being spaced from said front edge a distance of about 15 percent to about 40 percent of the total length of said device, said folded sheet further defining a generally centrally located pocket whereby said partial funnel-shaped portion serves to direct any fluid discharged directed thereat into said pocket.

16. The method of claim 15 further comprising the step of securing said contacting portions of said body side surface on opposite sides of said first diverging fold lines together.

17. A perineal shield and discharge containment device formed according to the method of claim 15.

* * * * *